(12) United States Patent
Dane et al.

(10) Patent No.: US 7,523,827 B2
(45) Date of Patent: Apr. 28, 2009

(54) ORTHOPAEDIC INSTRUMENT STERILIZATION CASE

(75) Inventors: Gary T. Dane, Bow, NH (US); Daniel L. Sands, Warsaw, IN (US); Jason K. Hawkes, Weare, NH (US)

(73) Assignee: Symmetry Medical, Inc., Warsaw, IN (US)

( * ) Notice: Subject to any disclaimer, the term of this patent is extended or adjusted under 35 U.S.C. 154(b) by 377 days.

(21) Appl. No.: 10/685,247

(22) Filed: Oct. 14, 2003

(65) Prior Publication Data

US 2004/0129595 A1 Jul. 8, 2004

Related U.S. Application Data

(60) Provisional application No. 60/418,528, filed on Oct. 15, 2002, provisional application No. 60/485,353, filed on Jul. 7, 2003.

(51) Int. Cl.
*B65D 21/032* (2006.01)

(52) U.S. Cl. ............... 206/503; 220/4.27; 206/508; 206/510

(58) Field of Classification Search ............... None
See application file for complete search history.

(56) References Cited

U.S. PATENT DOCUMENTS

| | | | | |
|---|---|---|---|---|
| 224,490 A | * | 2/1880 | Sturges | 312/201 |
| 3,529,878 A | | 9/1970 | Blowers | 312/107 |
| 4,600,103 A | * | 7/1986 | Tabler | 206/505 |
| 4,716,025 A | | 12/1987 | Nichols | 422/310 |
| 5,078,460 A | * | 1/1992 | Holsinger | 312/244 |
| 5,111,939 A | * | 5/1992 | Schafer | 206/503 |
| 5,287,980 A | * | 2/1994 | Saltz | 220/4.27 |
| 5,424,047 A | | 6/1995 | Zwingenberger et al. | 422/296 |
| 5,518,139 A | * | 5/1996 | Trower et al. | 220/522 |
| 5,540,901 A | | 7/1996 | Riley | 422/300 |
| 5,680,957 A | * | 10/1997 | Liu | 220/663 |
| 5,740,906 A | | 4/1998 | Lai | 206/214 |
| 5,882,097 A | * | 3/1999 | Kohagen et al. | 312/235.1 |
| 5,893,618 A | | 4/1999 | LePage, Jr. et al. | 312/265.6 |
| 6,116,452 A | | 9/2000 | Hamel et al. | 220/318 |
| 6,164,738 A | | 12/2000 | Dane et al. | 312/311 |
| 6,368,565 B1 | | 4/2002 | Michaelson et al. | 422/300 |
| 6,395,234 B1 | * | 5/2002 | Hunnell et al. | 422/101 |
| 6,896,149 B1 | | 5/2005 | Berry, III | 220/4.28 |
| 2002/0064490 A1 | | 5/2002 | Michaelson et al. | 422/300 |

* cited by examiner

*Primary Examiner*—Stephen Castellano
(74) *Attorney, Agent, or Firm*—Taylor & Aust, P.C.

(57) ABSTRACT

A sterilization case assembly including a plurality of sterilization cases having a first sterilization case and a second sterilization case. The second sterilization case is stacked upon the first sterilization case in a vertical direction. The second sterilization case is offset from the first sterilization case in a direction transverse to the vertical direction.

20 Claims, 5 Drawing Sheets

ORTHOPAEDIC INSTRUMENT STERILIZATION CASE

CROSS REFERENCE TO RELATED APPLICATIONS

This is a non-provisional application based upon U.S. provisional patent application Ser. No. 60/418,528, entitled "ORTHOPAEDIC INSTRUMENT STERILIZATION CASE", filed Oct. 15, 2002 and U.S. provisional patent application Ser. No. 60/485,353, entitled "ORTHOPAEDIC INSTRUMENT STERILIZATION CASE", filed Jul. 7, 2003.

BACKGROUND OF THE INVENTION

1. Field of the Invention

The present invention relates to sterilization cases and, more particularly, to orthopaedic instrument sterilization cases.

2. Description of the Related Art

Sterilization containers are known that provide organization, storage and sterilization functionality for surgical instruments and devices. In order to avoid infection to a patient on which such instruments used, the instruments are required to be cleaned and sterilized after a procedure, and therefore, before use.

Surgical procedures are regularly performed using "sets" of pre-selected surgical instruments, each set being a collection of instruments established from experience or design to be useful in a given surgical procedure. The surgical instruments expected to be used in a particular procedure are grouped together to form a set, and, as a set, are sterilized, stored on a pan or tray, and finally transported on that pan or tray to the operating room when their use is required. Complex procedures typically involve a substantial number of instruments. Thus, typically, several instrument trays may be necessary to accommodate all of the required surgical instruments. Accordingly, sterilizing cases often are designed to accommodate a plurality of trays with the instruments arranged on the trays in such a manner that the trays may be accessed as the surgical procedure advances often in a preset sequence.

An example of a cleaning procedure can be the instruments are first placed into a tank containing water and perhaps solvents, and ultrasound is applied to agitate the fluid to wash and remove the debris, such as biomatter, remaining on the instruments from their last use. The instruments are then sterilized in some manner to destroy any microorganisms, viruses or other contamination on the hand instruments. The two sterilization methods include the use of dry heat, wherein the instruments are heated to a high temperature, for example at least 365° Fahrenheit for a period of time, or the use of steam under pressure in an autoclave system. The time to sterilize, using a steam autoclave system, depends on heat and pressure and whether the instruments are wrapped or not. In some sterilization processes, chemicals are applied to the hand instruments as an intermediate step between the ultrasonic bath and the heating. A third method of sterilization is a chemical autoclave wherein a controlled atmosphere of various gases is used, with heat and humidity in some instances, to sterilize the instruments held within sealed sterile wraps. Radiation can also be used to sterilize instruments. In the situation of instruments in a sterilization case, a sterile wrap can cover the case to maintain the sterile field within the case after sterilization.

Major surgeries such as hip or knee replacements have larger instruments requiring multiple cases and trays of instruments. Sterilization systems are known which have multiple trays in a drawer arrangement, however when a tray is pulled forward to access the instruments, there is a shift in center of gravity forward which can cause the system to become unstable and tilt forward. Braces are known which rotate forward to stabilize such a sterilization case. Such braces, when in a stabilizing position, increase the footprint of the sterilization case on the table in the operating room.

What is needed in the art is an easily configurable sterilization system which does not become unstable when accessing instruments, which can accommodate large and complex instrument sets and which minimizes the sterilization container footprint while maximizing access to the instruments.

SUMMARY OF THE INVENTION

The present invention provides sterilization container which are configurable into a multiple level, stair step stacked, self-contained and self-standing instrument case for sterilizing, organizing, containing and transporting of surgical instruments and devices.

The invention comprises, in one form thereof, a sterilization case assembly including a plurality of sterilization cases having a first sterilization case and a second sterilization case. The second sterilization case is stacked upon the first sterilization case in a vertical direction. The second sterilization case is offset from the first sterilization case in a direction transverse to the vertical direction.

An advantage of the present invention is an easily configurable sterilization system which does not become unstable when accessing instruments.

Another advantage of the present invention is a sterilization system which can accommodate large and complex instrument sets and which minimizes the sterilization system footprint while maximizing access to the instruments.

Yet another advantage of the present invention is a stair step type stacking of individual cases acts to offset center of gravity shifts to prevent tipping when accessing instruments.

A further advantage of the present invention is a slidable modular mounting that allows removal of a tray from a drawer.

A further advantage of the present invention is four to six levels of sterilization trays stacked vertically will only require/occupy the same space that was once used by fewer trays.

A further advantage of the present invention is that the amount of space required in the operating room for sterilization cases and trays is decreased.

A further advantage of the present invention is that it enables a secure modular arrangement of single level trays of instruments that improves organization, presentation, access and deployment of instruments.

Another advantage of an embodiment of the present invention is a hinged front cover which locks in the open position to provide additional stabilization to prevent tipping.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
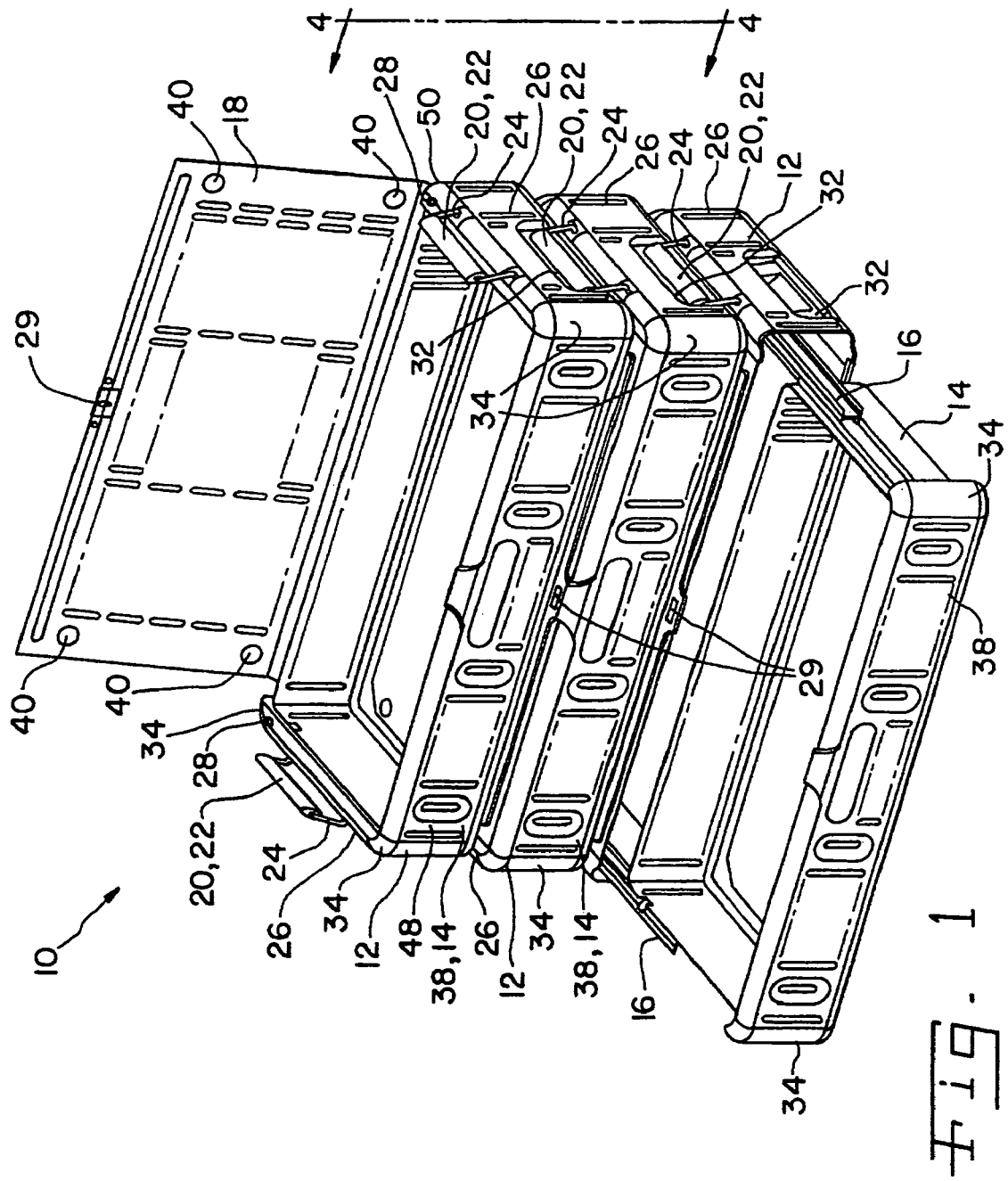
FIG. 1 is a perspective view of an embodiment of a multiple level sterilization system of the present invention, including 3 stacked cases.

Referring now to the drawings, and more particularly to FIG. 1, there is shown a stacked sterilization case assembly or system 10 which generally includes a plurality of sterilization cases 12, and in the embodiment shown, specifically three sterilization cases 12. Each sterilization case 12 includes at least one drawer 14 therein and attached to sterilization case 12 using slide mechanisms 16. Each sterilization case 12 includes lid 18 which can pivot open as shown. As will be subsequently discussed in detail, only one of drawer 14 or lid 18 can be open for a given sterilization case 12. The trays are interlocked using at least one handle 20 that can be located on both of the side of the trays. At least one sterilization case 12 is offset from another sterilization case 12 in a direction transverse to the vertical direction such as a frontward to reward direction as shown in the drawings.

Figure 2:
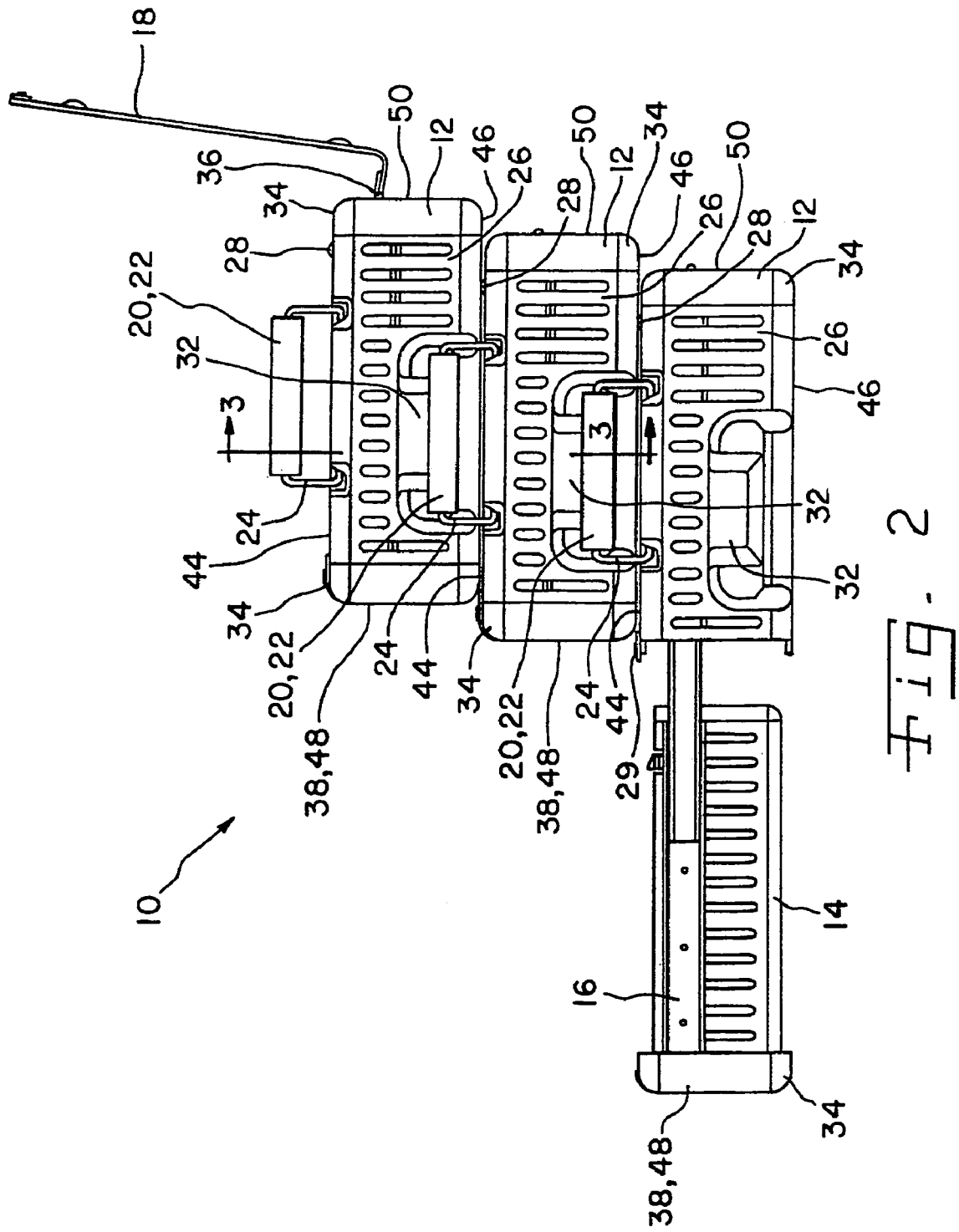
FIG. 2 is a side view of the multiple level sterilization case of FIG. 1.
Figure 3:
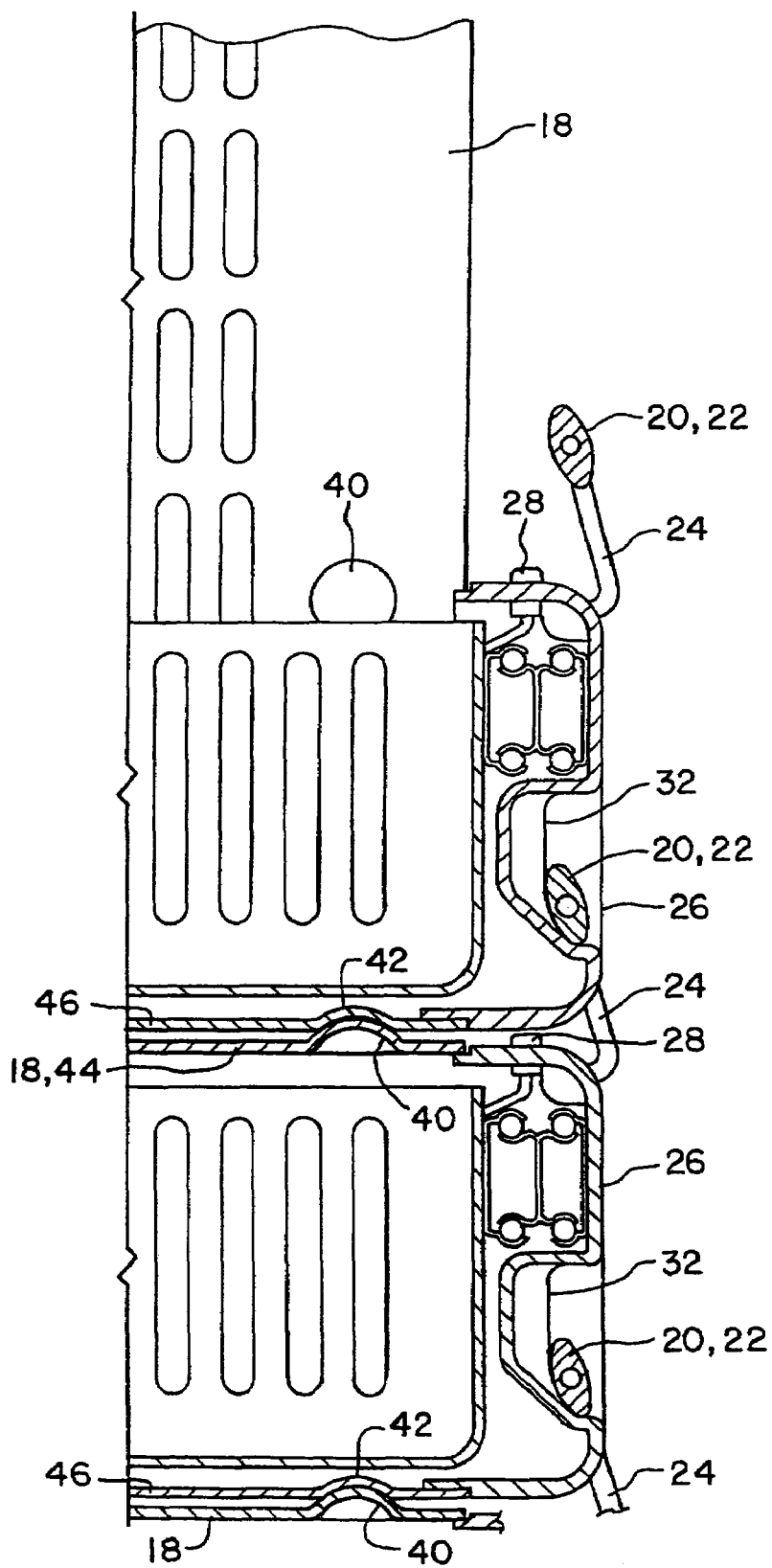
FIG. 3 is a fragmentary cross-sectional view taken along section line 3-3 of FIG. 2.
Figure 4:
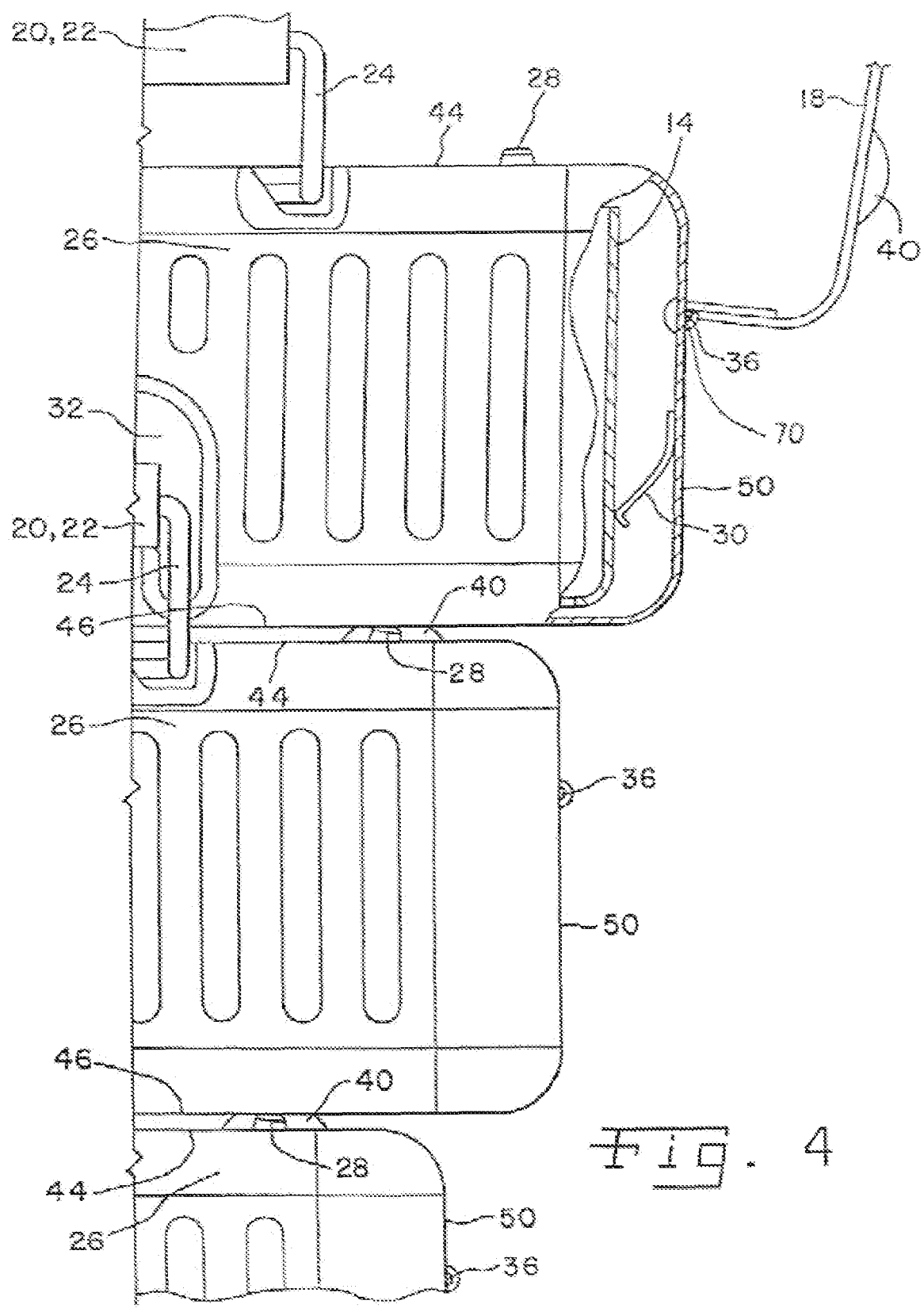
FIG. 4 is a partially fragmentary side view as viewed along section line 4-4 of FIG. 1.

FIG. 2 illustrates how the offset stacking features conserve back table space and help prevent tipping as drawers are opened and closed. As shown, lid 18 is capable of rotation, whereas drawer 14 is capable of translation. Lid 18 can rotate about a generally horizontal axis 70, which is shown in FIG. 4 to be coaxial with take-away hinge 36 and perpendicular to the plane of the page of FIG. 4.

Ergonomic handle grips 22 can be soft and cool to the touch. Unique bail 24 shape allows handles to lay flat on a case top or swing upward to facilitate proper removal technique from closed container systems. Resilient handle grips 22 roll flat in the palm of the hand for comfortable lifting and roll over center and into end cap 26 to lock stacked cases together.

Safety catch 28 prevents drawer 14 from opening in sterilization case 12 unless another sterilization case 12 is stacked upon it. The contents of a single case or the top case in a stack are accessed by opening lid 18. Safety catch 28 allows a drawer to be released in a sterilization case 12 having another sterilization case 12 stacked upon it when safety catch 28 is actuated. Latch 29 interlocks lid 18 and drawer 14, and when slid towards the back (away from the drawer front) of sterilization case 12, depending on the state of safety catch 28 and whether another case is on lid 18, one of drawer 14 or lid 18 will open.

The present invention can include assist spring 30 that slightly opens drawer 14 of a lower stacked case, or lid 18 of single cases or the top case in a stack. Assist spring 30 is shown for drawer 14, the assist spring 30 for a lid can be similar to what is shown, but positioned differently to actuate lid 18. Assist spring 30 can be a variety of resilient members such as other spring types (coil spring, etc.), rubber items and flexible containers with compressible liquids therein. Assist spring 30 facilitates easy opening of drawers 14 and lids 18. Drawers 14 can hold plastic trays by their rims and metal inserts as drop-ins, such trays and inserts holding sets of instruments (all not shown).

The size and shape of sterilization case 12 is wrap and container friendly and features resilient carrying handles 20 and recessed carrying pockets 32 in end panels 26. Rounded corners 34 are less likely to puncture a sterile wrap than sharp corners.

Take-away hinges 36 allow removal of the lid for access or cleaning purposes. End panels 26 can be cast from aluminum, titanium or other suitable metals, or injection molded from Radel, PEEK or other suitable plastics or materials.

Slider mechanisms 16 can be stainless steel or other suitable materials and can be rated to hold 40 lbs per pair, although different load carrying capacity is possible based on the expected use of sterilization system 10. Drawer front 38 can be drawn from aluminum or vacuum formed from Radel or made from other suitable materials. The highly perforated design with open drawer bottom and ability to access contents from the top or through an open drawer ensures unsurpassed cleanability and sterilization and safe access to contents.

The top 44 of sterilization case 12, or lid 18, includes at least one top registration element 40. Bottom 46 of sterilization case 12 includes at least one bottom registration element 42. At least one top registration element 40 is offset from at least one bottom registration element 42 in a direction parallel with bottom 46, or alternatively, lid 18 when closed. For example, sterilization case 12 includes opposed sides, first side 48 and second side 50, connected to bottom 46. At least one bottom registration element 42 is closer to one opposed side than at least one top registration element 40.

Figure 5:
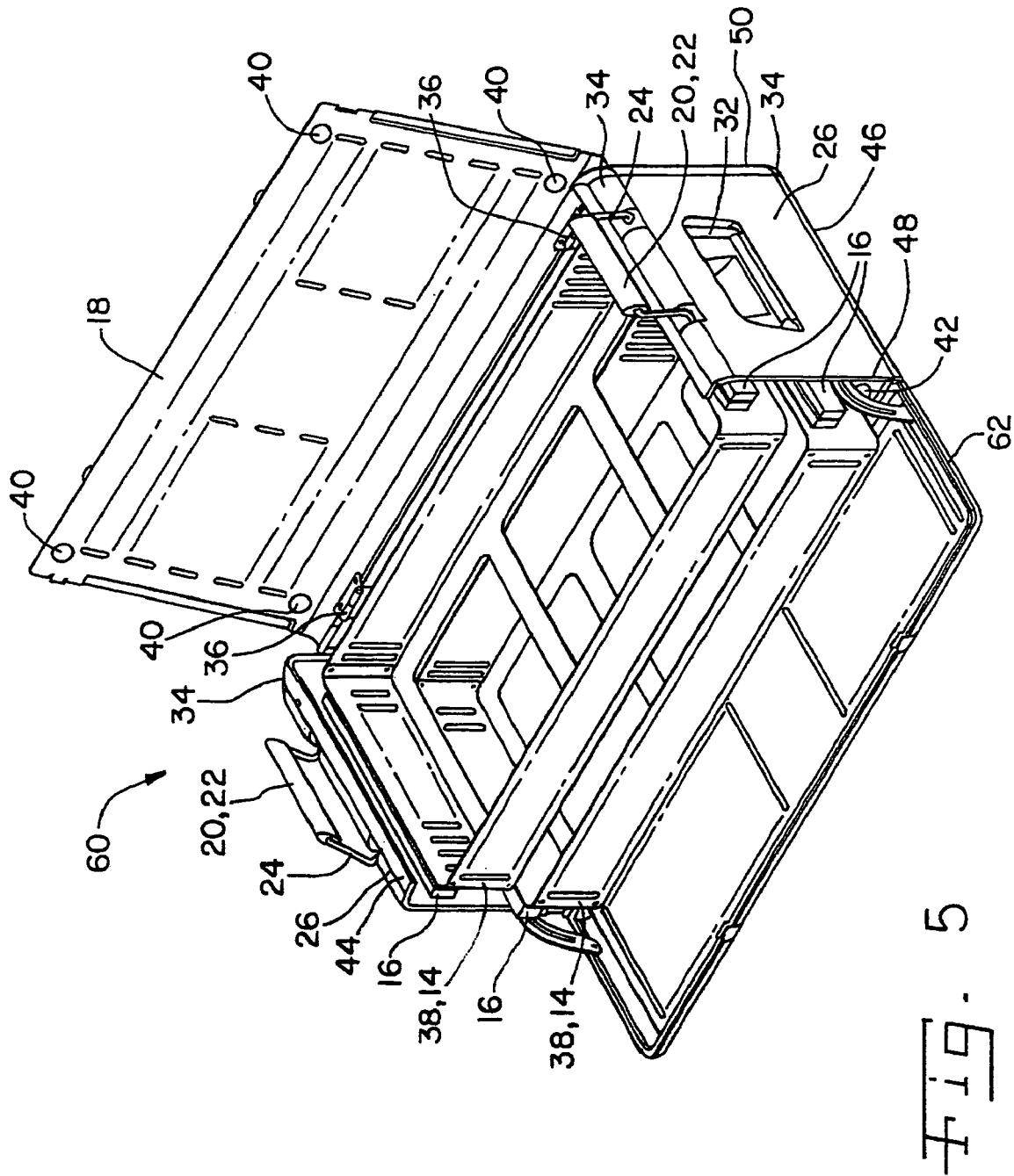
FIG. 5 is a perspective view of another embodiment of a stackable sterilization case having multiple trays.

In another embodiment (FIG. 5), sterilization case 60 includes a plurality of drawers 14 and hinged front cover 62. Hinged front cover 62 can also be lockable. Sterilization case 60 can be offset stacked similarly to sterilization case 12. Other features are similar to as already described and have been given identical reference characters. Sterilization case 60 may be more suitable for a hip or knee replacement surgery whereas sterilization case 12 may be more suitable for spinal or extremities surgery.

In use, a second sterilization case 12 is stacked upon a first sterilization case 12 in a vertical direction, and concurrently, the second sterilization case 12 is offset from the first sterilization case 12 in a direction transverse to the vertical direction. The second sterilization case 12 can be interlocked with the first sterilization case 12 using handles 20 and corresponding recessed pockets 32.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A sterilization case assembly, comprising:
   a plurality of sterilization cases including a first sterilization case and a second sterilization case, said second sterilization case stacked directly upon said first sterilization case in a vertical direction, said second sterilization case offset from said first sterilization case in a frontward to rearward direction, each of said plurality of sterilization cases being selectively movable between a closed position and an open position, said second sterilization case offset from said first sterilization case in a direction transverse to said vertical direction when each of said first and said second sterilization cases is in said closed position, in said closed position each of said plurality of sterilization cases having a general box shape and including a plurality of walls defining said general box shape, in said closed position said plurality of walls of each of said plurality of sterilization cases including a top wall and a bottom wall, said top wall and said bottom wall of each of said plurality of sterilization cases being substantially parallel relative to one another in said closed position and substantially horizontal in said closed position, said bottom wall of said second sterilization case at least partially directly contacting said top wall of said first sterilization case when each of said first and said second sterilization cases is in said closed position, said first and said second sterilization cases being substantially identical to one another when each of said first and said second sterilization cases is in said closed position, each of said plurality of sterilization cases including at least one drawer therein selectively slidable from said closed position to said open position in a rearward to frontward direction, said bottom wall of said second sterilization case being offset from said top wall of said first sterilization case in said frontward to rearward direction when each of said first and second sterilization cases is in said closed position and when said second sterilization case is seated on said first sterilization case, wherein each of said plurality of sterilization cases includes a front wall, a rear wall, and two opposing side walls, each said drawer including a side wall, each said front wall, rear wall, opposing side walls, and side wall of said drawer defines a plurality of holes configured for permitting sterilization of at least one surgical instrument contained in a respective said drawer.

2. The sterilization case assembly of claim 1, wherein at least one said case includes a plurality of said drawers.

3. The sterilization case assembly of claim 2, wherein said at least one case that includes a plurality of drawers has a hinged front cover.

4. The sterilization case assembly of claim 1, wherein said second sterilization case includes a hinged lid.

5. The sterilization case assembly of claim 4, wherein said lid is removable and rotates about a generally horizontal axis.

6. The sterilization case assembly of claim 4, wherein said first sterilization case includes at least one handle, said second sterilization case includes at least one recessed pocket, at least one said handle interlocks with at least one said recessed pocket when said second sterilization case is stacked upon said first sterilization case in a vertical direction.

7. The sterilization case assembly of claim 1, wherein in said closed position said plurality of walls of each of said plurality of sterilization cases includes said front wall and said rear wall, said front wall and said rear wall of each of said plurality of sterilization cases being substantially parallel relative to one another in said closed position, said front wall of said second sterilization case being transversely offset from and substantially parallel to said front wall of said first sterilization case when each of said first and said second sterilization cases is in said closed position, said rear wall of said second sterilization case being transversely offset from and substantially parallel to said rear wall of said first sterilization case when each of said first and said second sterilization cases is in said closed position.

8. The sterilization case assembly of claim 1, wherein said plurality of walls of each of said plurality of sterilization cases includes said rear wall oriented generally vertically rear wall coupled with said top and bottom walls, said top wall including at least one partially spherical top registration element, said bottom wall including at least one partially spherical bottom registration element, said top registration element being closer to said rear wall than said bottom registration element when each of said first and said second sterilization cases is in said closed position, said bottom registration element of said second sterilization case directly contacting said top registration element of said first sterilization case.

9. The sterilization case assembly of claim 1, wherein each of said plurality of sterilization cases is configured for providing organization, storage, and sterilization for at least one surgical instrument contained therein, said second sterilization case being offset from said first sterilization case in order to provide stability to said first and second sterilization cases when said second sterilization case is stacked on said first sterilization case and any of said plurality of drawers are slid to said open position.

10. The sterilization case assembly of claim 1, wherein said second sterilization case is offset from said first sterilization case in said frontward to rearward direction such that said first and second sterilization cases form a stair-stepped stack of said plurality of sterilization cases so as to provide stability to said stair-stepped stack and to offset a center of gravity forward shift of said stair-stepped stack and thereby to prevent tipping of said stair-stepped stack when said drawer of said second sterilization case is slid to said open position, said second sterilization case being offset from said first sterilization case in said frontward to rearward direction such that said stair-stepped stack is self supporting when any of said drawers of said plurality of sterilization cases is in said open position.

11. The sterilization case assembly of claim 1, wherein said bottom wall of said second sterilization case is offset from said top wall of said first sterilization case in said frontward to rearward direction when said first and second sterilization cases are engaged relative to one another.

12. A sterilization case assembly, comprising:
a plurality of sterilization cases including a first sterilization case and a second sterilization case, said second sterilization case offset from said first sterilization case in a frontward to rearward direction, said first sterilization case including at least one handle, said second sterilization case including at least one recessed pocket, at least one said handle interlocking with at least one said recessed pocket when said second sterilization case is stacked directly upon said first sterilization case in a vertical direction, each of said plurality of sterilization cases being selectively movable between a closed position and an open position, said second sterilization case being offset from said first sterilization case in a direction transverse to said vertical direction when each of said first and said second sterilization cases is in said closed position, in said closed position each of said plurality of sterilization cases having a general box shape and including a plurality of walls defining said general box shape, in said closed position said plurality of walls of each of said plurality of sterilization cases including a top wall and a bottom wall, said top wall and said bottom wall of each of said plurality of sterilization cases being substantially parallel relative to one another in said closed position and substantially horizontal in said closed position, said bottom wall of said second sterilization case at least partially directly contacting said top wall of said first sterilization case when said second sterilization case is stacked upon said first sterilization case in a vertical direction and when each of said first and said second sterilization cases is in said closed position, each of said plurality of sterilization cases including at least one drawer therein selectively slidable from said closed position to said open position in a rearward to frontward direction, said bottom wall of said second sterilization case being offset from said top wall of said first sterilization case in said frontward to rearward direction when each of said first and second sterilization cases is in said closed position and when said second sterilization case is seated on said first sterilization case, wherein each of said plurality of sterilization cases includes a front wall, a rear wall, and two opposing side walls, each said drawer including a side wall, each said front wall, rear wall, opposing side walls, and side wall of said drawer defines a plurality of holes configured for permitting sterilization of at least one surgical instrument contained in a respective said drawer.

13. The sterilization case assembly of claim 12, wherein said plurality of walls of each of said plurality of sterilization cases includes said rear wall oriented generally vertically rear wall coupled with said top and bottom walls, said top wall including at least one partially spherical top registration element, said bottom wall including at least one partially spherical bottom registration element, said top registration element being closer to said rear wall than said bottom registration element when each of said first and said second sterilization cases is in said closed position, said bottom registration element of said second sterilization case directly contacting said top registration element of said first sterilization case.

14. The sterilization case assembly of claim 12, wherein said second sterilization case is offset from said first sterilization case in said frontward to rearward direction such that said first and second sterilization cases form a stair-stepped stack of said plurality of sterilization cases so as to provide stability to said stair-stepped stack and to offset a center of gravity forward shift of said stair-stepped stack and thereby to prevent tipping of said stair-stepped stack when said drawer of said second sterilization case is slid to said open position, said second sterilization case being offset from said first sterilization case in said frontward to rearward direction such that said stair-stepped stack is self-supporting when any of said drawers of said plurality of sterilization cases is in said open position.

15. The sterilization case assembly of claim 12, wherein said bottom wall of said second sterilization case is offset from said top wall of said first sterilization case in said frontward to rearward direction when said first and second sterilization cases are engaged relative to one another.

16. A method of assembling a sterilization case assembly, comprising the steps of:
stacking a plurality of sterilization cases including a first sterilization case and a second sterilization case, said second sterilization case stacked directly upon said first sterilization case in a vertical direction;
offsetting said second sterilization case from said first sterilization case in a frontward to rearward direction;
providing both said first and said second sterilization cases are selectively movable between a closed position and an open position, each of said plurality of sterilization cases including at least one drawer therein selectively slidable from said closed position to said open position in a rearward to frontward direction;
providing that in said closed position each of said first and said second sterilization cases has a general box shape and includes a plurality of walls defining said general box shape, in said closed position said plurality of walls of each of said first and said second sterilization cases including a top wall and a bottom wall, said top wall and said bottom wall of each of said first and said second sterilization cases being substantially parallel relative to one another in said closed position and substantially horizontal in said closed position, said bottom wall of said second sterilization case at least partially directly contacting said top wall of said first sterilization case when said second sterilization case is stacked upon said first sterilization case in a vertical direction and when each of said first and said second sterilization cases is in said closed position; and
offsetting said second sterilization case from said first sterilization case in a direction transverse to said vertical direction when each of said first and said second sterilization cases is in said closed position, said first and said second sterilization cases being substantially identical to one another when each of said first and said second sterilization cases is in said closed position, said bottom wall of said second sterilization case being offset from said top wall of said first sterilization case in said frontward to rearward direction when each of said first and second sterilization cases is in said closed position and when said second sterilization case is seated on said first sterilization case, wherein each of said plurality of sterilization cases includes a front wall, a rear wall, and two opposing side walls, each said drawer including a side wall, each said front wall, rear wall, opposing side walls, and side wall of said drawer defines a plurality of holes configured for permitting sterilization of at least one surgical instrument contained in a respective said drawer.

17. The method of claim 16, further including the step of interlocking said second sterilization case with said first sterilization case.

18. The sterilization case assembly of claim 16, wherein said plurality of walls of each of said plurality of sterilization cases includes said rear wall oriented generally vertically rear wall coupled with said top and bottom walls, said top wall including at least one partially spherical top registration element, said bottom wall including at least one partially spherical bottom registration element, said top registration element being closer to said rear wall than said bottom registration element when each of said first and said second sterilization cases is in said closed position, said bottom registration element of said second sterilization case directly contacting said top registration element of said first sterilization case.

19. The method of claim 16, wherein said second sterilization case is offset from said first sterilization case in said frontward to rearward direction such that said first and second sterilization cases form a stair-stepped stack of said plurality of sterilization cases so as to provide stability to said stair-stepped stack and to offset a center of gravity forward shift of said stair-stepped stack and thereby to prevent tipping of said stair-stepped stack when said drawer of said second sterilization case is slid to said open position, said second sterilization case being offset from said first sterilization case in said frontward to rearward direction such that said stair-stepped stack is self-supporting when any of said drawers of said plurality of sterilization cases is in said open position.

20. The method of claim 16, wherein said bottom wall of said second sterilization case is offset from said top wall of said first sterilization case in said frontward to rearward direction when said first and second sterilization cases are engaged relative to one another.

* * * * *